United States Patent [19]
Yokoe et al.

[11] Patent Number: 5,033,471
[45] Date of Patent: Jul. 23, 1991

[54] METHOD AND APPARATUS MEASURING BLOOD PRESSURE

[75] Inventors: Hifumi Yokoe, Kosai; Norio Kawamura, Nagoya, both of Japan

[73] Assignee: Colin Electronics Co., Ltd., Japan

[21] Appl. No.: 325,983

[22] Filed: Mar. 20, 1989

[30] Foreign Application Priority Data

Mar. 23, 1988 [JP] Japan .................................. 63-69140

[51] Int. Cl.5 .............................................. A61B 5/021
[52] U.S. Cl. .................................................. 128/681
[58] Field of Search ......................... 128/672, 677-690

[56] References Cited

U.S. PATENT DOCUMENTS

| 4,669,485 | 6/1987 | Russell | 128/681 X |
| 4,697,596 | 10/1987 | Link | 128/677 X |
| 4,799,491 | 1/1989 | Eckerle | 128/690 X |
| 4,799,492 | 1/1989 | Nelson | 128/672 |

Primary Examiner—William E. Kamm
Attorney, Agent, or Firm—Oliff & Berridge

[57] ABSTRACT

A method and an apparatus for measuring blood pressure of a subject by using a pulse wave sensor for detecting pulse wave produced from an arterial vessel of the subject, and pressing device for pressing the pulse wave sensor against the arterial vessel via a body surface of the subject, the method comprising the steps of pressing the pulse wave sensor against the arterial vessel with a continuously variable pressing force produced by the pressing device, detecting variation in magnitude of the pulse wave with the pulse wave sensor while the pressing force of the pressing device is continuously varied, and determining blood pressure of the subject based on the detected magnitude variation of the pulse wave.

19 Claims, 3 Drawing Sheets

METHOD AND APPARATUS MEASURING BLOOD PRESSURE

BACKGROUND OF THE INVENTION

1. Field of the Invention

The present invention relates to a method and an apparatus for measuring blood pressure of a subject based on pulse wave detected by a pulse wave sensor pressed against an arterial vessel.

2. Discussion of the Prior

There is known the "oscillometric" method as a method of measuring blood pressure. In the oscillometric method, a bag-like, rubber inflatable cuff is set around an upper arm of a subject, and pressurized air is supplied to the cuff to increase pressure in the cuff (hereinafter, referred to as 'cuff pressure') and thereby press the upper arm, so that pulse wave, i.e., oscillatory pressure wave produced synchronously with heartbeat of the subject is detected while the pressure in the cuff is increased. Blood pressure of the subject is determined based on the detected magnitude variation of the pulse wave.

In the above-indicated conventional method, an inflatable cuff is used for pressing the upper arm or other body portions of the subject. The cuff has a comparatively large size or volume, and therefore is bothersome to the subject, particularly in the case where the cuff is maintained on the body portion for a long time. Furthermore, since the cuff has a bag-like structure and, when used, is wound around the body portion of the subject, the cuff pressure tends to be adversely influenced by, for example, physical motion of the subject. In such case, the accuracy of blood pressure measurement is deteriorated.

In the case where the cuff is maintained around the body portion of the subject to monitor, i.e., continuously measure blood pressure of the subject for a comparatively long period after a surgical operation, for example, the subject may suffer from congestion and/or uncomfortable feeling because the body portion continues to be pressed with considerable force for that period.

SUMMARY OF THE INVENTION

It is therefore an object of the present invention to provide a method and an apparatus for measuring blood pressure of a subject, in which blood pressure is measured by using a pulse wave sensor and means for pressing the pulse wave sensor against an arterial vessel, and an inflatable cuff is not used.

According to a first aspect of the present invention, there is provided a method of measuring blood pressure of a subject by using a pulse wave sensor for detecting pulse wave produced from an arterial vessel of the subject, and pressing means for pressing the pulse wave sensor against the arterial vessel via a body surface of the subject, the method comprising the steps of (a) pressing the pulse wave sensor against the arterial vessel with a continuously variable pressing force produced by the pressing means, (b) detecting variation in magnitude of the pulse wave with the pulse wave sensor while the pressing force of the pressing means is continuously varied, and (c) determining blood pressure of the subject based on the detected magnitude variation of the pulse wave.

In the blood pressure measuring method arranged as described above, magnitude variation of the pulse wave is detected by the pulse wave sensor while pressing force of the pressing means is continuously varied, and blood pressure of the subject is determined based on the detected magnitude variation of the pulse wave. Since the blood pressure is determined based on the magnitude variation of pulse wave detected by the pulse wave sensor pressed against the arterial vessel by the pressing means, the present method does not require an inflatable cuff, in contrast to conventional blood pressure measuring methods. Thus, the present method eliminates cumbersome activities required to set the cuff around a body portion of a subject, and permits accurate blood pressure measurement free from adverse influence of noise resulting from physical motion of a subject.

According to a feature of the above method, the pulse wave consists of a plurality of pulses, and the step of detecting variation in magnitude of the pulse wave consists of detecting an amplitude of each of the pulses of the pulse wave. In this case, it is preferred that the step of determining blood pressure of the subject consists of selecting, from the detected pulses of the pulse wave, a rising pulse whose amplitude has significantly largely changed, determining a pressing force of the pressing means at a time of detection of the rising pulse, and determining blood pressure of the subject based on the determined pressing force according to a predetermined relationship between blood pressure and the pressing force of the pressing means.

According to a second aspect of the present invention, there is provided a method of continuously measuring blood pressure of a subject by using a pulse wave sensor for detecting pulse wave produced from an arterial vessel of the subject, and pressing means for pressing the pulse wave sensor against the arterial vessel via a body surface of the subject, the pulse wave consisting of a plurality of pulses, the method comprising the steps of (1) pressing the pulse wave sensor against the arterial vessel with a continuously variable pressing force produced by the pressing means, (2) detecting variation in magnitude of pulses of the pulse wave with the pulse wave sensor while the pressing force of the pressing means is continuously varied, and (3) determining actual blood pressure of the subject based on the detected magnitude variation of the pulses of the pulse wave, (4) selecting, from the detected pulses of the pulse wave, a maximum pulse having a maximum amplitude, (5) maintaining the pressing force of the pressing means at an optimum force at which the maximum pulse has been detected by the pulse wave sensor while the pressing force is continuously varied, so that the pulse wave sensor is pressed against the arterial vessel with the optimum force and continuously detects optimum pulses of the pulse wave each of which has substantially the same amplitude as the maximum amplitude of the maximum pulse, (6) determining a relationship between blood pressure and pulse wave magnitude, based on the determined actual blood pressure and a magnitude of at least one pulse of the maximum pulse and the optimum pulses, and (7) continuously determining blood pressure of the subject according to the determined relationship based on magnitudes of the optimum pulses.

In the continuous blood pressure measuring method arranged as described above, magnitude variation of pulses of the pulse wave is detected by the pulse wave sensor while pressing force of the pressing means is continuously varied, and actual blood pressure of the subject is determined based on the detected magnitude variation of the pulses of the pulse wave. Further, the pressing force of the pressing means is maintained at an optimum force at which a maximum pulse having a maximum amplitude is detected by the pulse wave sensor while the pressing force is continuously varied, so that the pulse wave sensor is pressed against the arterial vessel with the optimum force and continuously detects optimum pulses of pulse wave each of which has substantially the same amplitude as that of the maximum pulse. A relationship between blood pressure and pulse wave magnitude is determined based on the determined actual blood pressure and a magnitude of at least one pulse of the maximum pulse and the optimum pulses. The thus determined relationship is utilized to continuously determine blood pressure of the subject based on magnitudes of the optimum pulses.

Since blood pressure is determined based on the magnitude variation of the pulses of pulse wave detected by the pulse wave sensor pressed against the arterial vessel by the pressing means, the instant method does not need an inflatable cuff, similar to the method according to the first aspect of the invention, in contrast to the conventional methods. Therefore, the instant method enjoys the same advantages as those of the method according to the first aspect.

As described above, the pressing force of the pressing means is maintained at the optimum force, so that the pulse wave sensor continuously detects optimum pulses of pulse wave, and a relationship between blood pressure and pulse wave magnitude is determined based on at least one pulse out of the maximum pulse and the optimum pulses in combination with the actual blood pressure, and blood pressure of the subject is continuously determined according to the thus determined relationship based on magnitudes of the optimum pulses. Thus, the instant method permits accurate continuous blood pressure measurement.

In a preferred embodiment of the method in accordance with the second aspect of the present invention, the step of determining a relationship between blood pressure and pulse wave magnitude, consists of determining a relationship between blood pressure and pulse wave magnitude based on the determined actual blood pressure and a magnitude of a first one of the optimum pulses, the first optimum pulse being detected by the pulse wave sensor immediately after the pressing force of the pressing means is fixed at the optimum force.

In another embodiment of the same method, the step of pressing the pulse wave sensor, the step of detecting variation in magnitude of pulses of the pulse wave, the step of determining actual blood pressure of the subject, the step of selecting a maximum pulse, the step of maintaining the pressing force at an optimum force, and the step of determining a relationship between blood pressure and pulse wave magnitude, are effected at each of a plurality of repetitive cycles, so that the relationship determined at each cycle is replaced with the relationship determined at a cycle following the each cycle, and the step of continuously determining blood pressure of the subject consists of continuously determining blood pressure of the subject according to a currently effective one of the repetitively determined relationships.

In the above embodiment, actual blood pressure is determined at each of the repetitive cycles based on the magnitude variation of the pulses of pulse wave which variation is detected by the pulse wave sensor while the pressing force of the pressing means is continuously varied, so that a relationship between blood pressure and pulse wave magnitude is determined at the cycle. Namely, the relationship is updated or adjusted at each cycle. Blood pressure of the subject is continuously determined according to a currently effective one of the repetitively determined relationships. Thus, the instant method assures a long time blood pressure monitoring without congestion and with extremely reduced uncomfortable feeling in a subject, in contrast to the conventional methods using an inflatable cuff which continues to press an upper arm or other portions of a subject to continuously measure blood pressure of the subject. It is preferred that the plurality of repetitive cycles have a predetermined cycle time, each of the repetitively determined relationships being effective during the predetermined cycle time, the predetermined cycle time falling in a range of 5 to 10 minutes.

In yet another embodiment of the same method of the invention, the step of determining actual blood pressure of the subject consists of determining actual maximum and minimum blood pressure of the subject, the step of determining a relationship between blood pressure and pulse wave magnitude consists of determining a relationship between blood pressure and pulse wave magnitude based on the actual maximum and minimum blood pressure and a maximum and a minimum magnitude of at least one pulse of the maximum pulse and the optimum pulses, and the step of continuously determining blood pressure of the subject consists of continuously determining maximum and minimum blood pressure of the subject according to the determined relationship based on maximum and minimum magnitudes of the optimum pulses.

In the above embodiment, it is preferred that the relationship between blood pressure and pulse wave magnitude be expressed as follows:

$$SYS = K \cdot m_{max} + a$$

$$DIA = K \cdot m_{min} + a$$

, wherein
SYS: maximum blood pressure of the subject,
DIA: minimum blood pressure of the subject,
K, a: constants,
$m_{max}$: maximum magnitude of each of the optimum pulses, and
$m_{min}$: minimum magnitude of each of the optimum pulses,
constants K, a being determined by replacing values SYS, DIA with the determined actual maximum and minimum blood pressure, respectively, and replacing values $m_{max}$, $m_{min}$ with the maximum and minimum magnitude of the at least one pulse of the maximum pulse and the optimum pulses, respectively.

According to a third aspect of the present invention, there is provided an apparatus for measuring blood pressure of a subject, comprising (a) a pulse wave sensor for detecting pulse wave produced from an arterial vessel of the subject, (b) pressing means for pressing the pulse wave sensor against the arterial vessel via a body surface of the subject, with a pressing force, the pulse wave sensor detecting variation in magnitude of the pulse wave while the pressing force of the pressing means is continuously varied, and (c) means for determining blood pressure of the subject based on the detected magnitude variation of the pulse wave.

The above apparatus offers the same advantages as those of the method according to the first aspect of the invention.

According to a fourth aspect of the invention, there is provided an apparatus for continuously measuring blood pressure of a subject, comprising (1) a pulse wave sensor for detecting pulse wave produced from an arterial vessel of the subject, the pulse wave consisting of a plurality of pulses, (2) pressing means for pressing the pulse wave sensor against the arterial vessel via a body surface of the subject, with a pressing force, (3) the pulse wave sensor detecting variation in magnitude of pulses of the pulse wave while the pressing force of the pressing means is continuously varied, (4) first means for determining actual blood pressure of the subject based on the detected magnitude variation of the pulses of the pulse wave, (5) second means for selecting, from the detected pulses of the pulse wave, a maximum pulse having a maximum amplitude, (6) third means for maintaining the pressing force of the pressing means at an optimum force at which the maximum pulse has been detected by the pulse wave sensor while the pressing force is continuously varied, so that the pulse wave sensor is pressed against the arterial vessel with the optimum force and continuously detects optimum pulses of the pulse wave each of which has substantially the same amplitude as the maximum amplitude of the maximum pulse, (7) fourth means for determining a relationship between blood pressure and pulse wave magnitude, based on the determined actual blood pressure and a magnitude of at least one pulse of the maximum pulse and the optimum pulses, and (8) fifth means for continuously determining blood pressure of the subject according to the determined relationship based on magnitudes of the optimum pulses.

The above apparatus provides the same advantages as those of the method according to the second aspect of the invention.

In a preferred embodiment of the apparatus according to the fourth aspect of the invention, the fourth means determines the relationship based on the determined actual blood pressure and a magnitude of a first one of the optimum pulses, the first optimum pulse being detected by the pulse wave sensor immediately after the pressing force of the pressing means is fixed at the optimum force.

In another embodiment of the same apparatus, the pressing means presses the pulse wave sensor at each of a plurality of repetitive cycles, the pulse wave sensor detects the magnitude variation of the pulses of the pulse wave at the each cycle, the first means determines the actual blood pressure at the each cycle, the second means selects the maximum pulse at the each cycle, the third means maintains the pressing force at the optimum force at the each cycle, the fourth means determines the relationship at the each cycle, the relationship determined at each cycle being replaced by the relationship determined at a cycle following the each cycle, and the fifth means continuously determines the blood pressure of the subject according to a currently effective one of the repetitively determined relationships. It is preferred that the plurality of repetitive cycles have a predetermined cycle time, each of the repetitively determined relationships being effective during the predetermined cycle time, the predetermined cycle time falling in a range of 5 to 10 minutes.

In yet another embodiment of the same apparatus of the invention, the pressing means comprises a housing in which the pulse wave sensor is accommodated, an elastic diaphragm disposed between the housing and the pulse wave sensor such that the pulse wave sensor is supported by the elastic diaphragm and that the elastic diaphragm cooperates with the housing to define a fluid-tight space in the housing, an elastic pump for supplying the fluid-tight space with pressurized fluid so as to increase pressure in the fluid-tight space, and a pressure-regulating valve for regulating the pressurized fluid in the fluid-tight space and thereby regulating the pressure of the fluid-tight space, the elastic diaphragm pressing the pulse wave sensor against the arterial vessel via the body surface while the pressure of the fluid-tight space is continuously varied, the pressure of the fluid-tight space serving as the pressing force of the pressing means. It is preferred that the pulse wave sensor detect the magnitude variation of the pulses of the pulse wave while the pressure of the fluid-tight space is continuously increased from 40 mmHg at a rate of 5 to 6 mmHg per second. The pulse wave sensor may detect the magnitude variation of the pulses of the pulse wave while the pressure of the fluid-tight space is continuously decreased from 180 mmHg at a rate of 5 to 6 mmHg per second.

According to a feature of the same apparatus, the continuous variation of the pressing force of the pressing means is terminated after the actual blood pressure is determined by the first means.

The apparatus according to the fourth aspect of the invention, may further comprises means for continuously displaying the blood pressure of the subject determined by the fifth means.

BRIEF DESCRIPTION OF THE DRAWINGS

The above and optical objects, features and advantages of the present invention will be better understood by reading the following detailed description of the presently preferred embodiment of the invention, when considered in conjunction with the accompanying drawings, in which.

DETAILED DESCRIPTION OF THE PREFERRED EMBODIMENT

Figure 1:
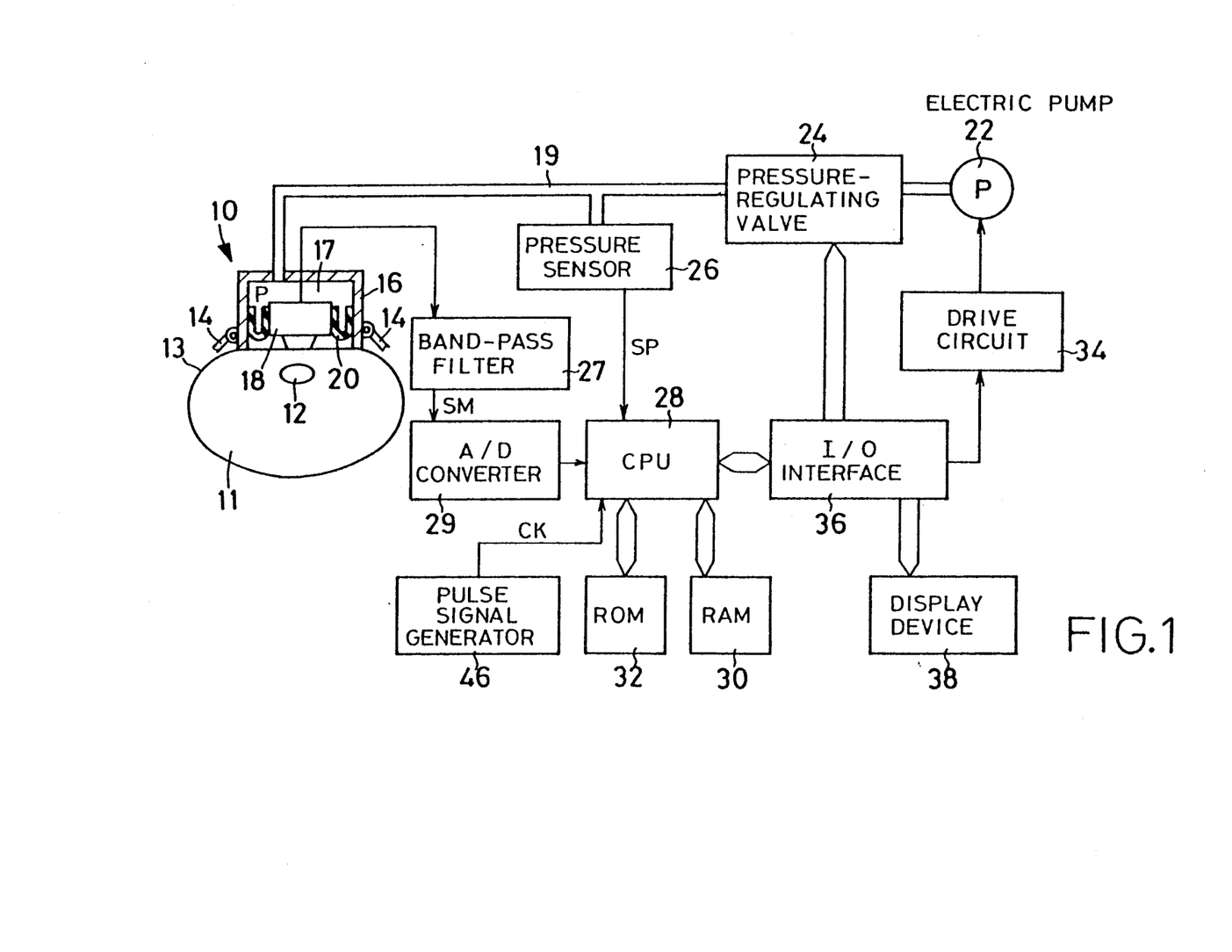
FIG. 1 is an illustrative view of a blood pressure monitoring apparatus embodying the present invention.

Referring first to FIG. 1, there is shown a blood pressure monitoring apparatus embodying the present invention. In the figure, reference numeral 10 designates a pulse wave detecting probe which is set on a surface 13 of a wrist 11 of a subject so as to be positioned above a radial artery 12 extending near a radius of the wrist 11. The probe 10 is fixed on the wrist surface 13 by winding and fastening a wrist band 14 around the wrist 11.

The pulse wave detecting probe 10 includes a rectangular container or housing 16, a pulse wave sensor 18 and an elastic diaphragm 20. The housing 16 is formed of a rigid material and has an opening in its bottom (as viewed in FIG. 1). The pulse wave sensor 18 is accommodated in the housing 16 such that, when the probe 10 is set on the wrist surface 13, the sensor 18 contacts the surface 13. The elastic diaphragm 20 is formed of rubber or the like, and is disposed between the pulse wave sensor 18 and side walls of the housing 16, such that the sensor 18 is secured to the housing 16 via the diaphragm 20 and that the diaphragm 20 cooperates with the housing 16 and pulse wave sensor 18 to define a fluid-tight space 17 in the housing 16.

The fluid-tight space 17 is supplied with pressurized fluid from an electrically operated pump 22 via a piping 19. A pressure-regulating valve 24 regulates the pressurized fluid in the fluid-tight space 17 and thereby regulates a pressure P in the space 17. The pressure-regulating valve 24 is selectively placed in a rapid-inflation position, a slow-inflation position and a holding position. In the rapid-inflation position the valve 24 permits pressure P to be increased at a high rate from zero mmHg to a target pressure Pm which is predetermined to be lower than an estimated minimum blood pressure of the subject, for example 40 mmHg. In the slow-inflation position the valve 24 permits pressure P to be increased at a slow rate which is suitable to detect pulse wave from the radial artery 12, for example 5 to 6 mmHg/sec. In the holding position the valve 24 permits pressure P to be maintained at an appropriate level. Further, the pressure-regulating valve 24 is placed in a rapid-deflation position in which the valve 24 permits pressure P to be decreased at a high rate.

A pressure sensor 26 is connected to the piping 19 at a location between the housing 16 (fluid-tight space 17) and the pressure-regulating valve 24, so that the sensor 26 detects pressure P in the space 17 and generates signal SP representative of the detected pressure P to a central processing unit (CPU) 28.

The pulse wave sensor 18 includes a semiconductor strain gauge or piezoelectric element for converting pulsation of an artery into electric signal. Upon supply of the pressurized fluid from the electric pump 22 to the fluid-tight space 17, pressure P of the fluid-tight space 17 is increased so that the elastic diaphragm 20 is expanded, whereby the pulse wave sensor 18 is pressed against the radial artery 12 via the wrist surface 13. The sensor 18 detects pulse wave, i.e., oscillatory pressure wave produced by expansion and contraction of the radial artery 12 synchronous with heartbeat of the subject, and generates signal SM representative of the detected pulse wave to the CPU 28 via a band-pass filter 27 and an analog-to-digital (A/D) converter 29. The pulse wave consists of a plurality of pulses. In the present embodiment, the housing 16, diaphragm 20, electric pump 22, pressure-regulating valve 24 and others cooperate with each other to serve as the means for pressing the pulse wave sensor against the arterial vessel via the body surface.

Figure 2A:
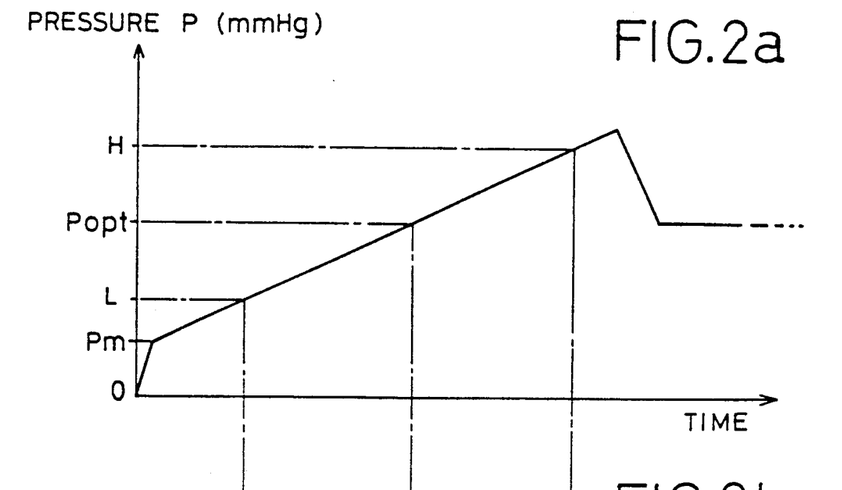
FIGS. 2(a) and 2(b) are graphs showing a time-wise variation in pressure of a fluid-tight space of a pulse wave detecting probe of the apparatus of FIG. 1, and a time-wise variation in magnitude of pulse wave detected by a pulse wave sensor of the probe, respectively.

The CPU 28 cooperates with a random access memory (RAM) 30 and a read only memory (ROM) 32 to constitute a microcomputer. The CPU 28 processes the received signals according to software programs pre-stored in the ROM 32 by utilizing temporary-storage function of the RAM 30, and effects operations for monitoring blood pressure of the subject. Specifically described, the CPU 28 generates ON/OFF signal via an input/output (I/O) interface 36 to a drive circuit 34 associated with the electric pump 22, so as to control supply of electric power from the drive circuit 34 to the electric pump 22 and thereby selectively activate and deactivate the pump 22. The CPU 28 also generates command signal to the pressure-regulating valve 24 via the I/O interface 36, so as to increase pressure P in the fluid-tight space 17 of the housing 16 at the high rate to target level Pm and subsequently increase at the slow rate. These steps are clearly shown in the graph of FIG. 2(a). While pressure P is increased at the slow rate, the CPU 28 operates to time-wise store in the RAM 30 variation in magnitude of pulses of the pulse wave represented by pulse wave signal SM in association with pressure P of the fluid-tight space 17 represented by pressure signal SP. The CPU 28 determines actual maximum blood pressure H and actual minimum blood pressure L of the subject based on variation in the magnitudes of the pulses and the pressure of the fluid-tight space 17, as described later.

Further, the CPU 28 selects, from the pulses of the pulse wave detected and stored while pressure P is increased at the slow rate, a maximum pulse $M_{max}$ which has a maximum amplitude in all the stored pulses, and determines as an optimum pressure $P_{opt}$ a pressure of the fluid-tight space 17 at the time of detection of maximum pulse $M_{max}$. These steps are clearly shown in the graphs of FIG. 2(a) and 2(b). After determining blood pressure H and L, the CPU 28 places the pressure-regulating valve 24 in the rapid deflation position so as to rapidly decrease pressure P and subsequently in the holding position so as to maintain pressure P at optimum pressure $P_{opt}$.

Figure 2B:
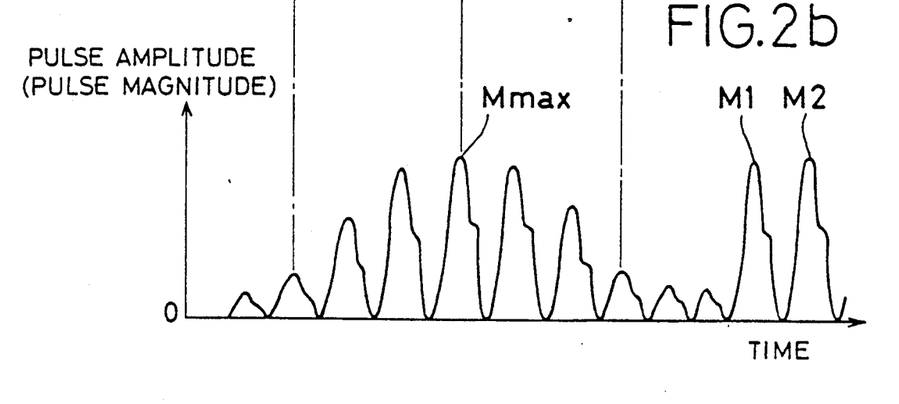
Figure 3:
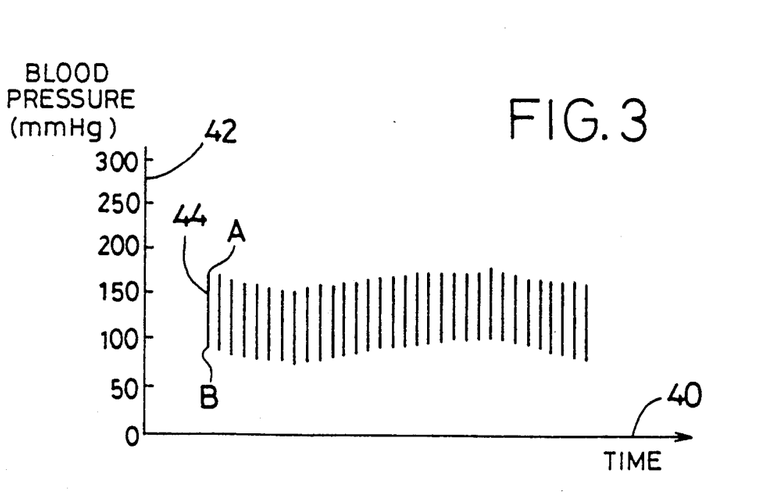
FIG. 3 is a graph showing a time-wise trend of blood pressure of a subject displayed on a display device of the apparatus of FIG. 1.

Moreover, the CPU 28 determines a relationship between blood pressure and pulse magnitude (hereinafter, referred to as BP-PM relationship), based on blood pressure H and L and an upper and a lower peak value, i.e., a maximum and a minimum magnitude of a first optimum pulse M1 (FIG. 2(b)). As shown in FIG. 2(b), the pulse wave sensor 18, which is currently pressed against the radial artery 12 with pressure P maintained at optimum pressure $P_{opt}$, continuously detects optimum pulses M1, M2, . . . each having substantially the same amplitude as that of maximum pulse $M_{max}$. The CPU 28 continuously estimates blood pressure of the subject according to the determined BP-PM relationship based on a maximum and a minimum magnitude of each of optimum pulses M2, . . . , and generates display signal to a display device 38 so as to continuously display the thus determined blood pressure. The display device 38 has a cathode ray tube on which is provided a two-dimensional table defined by an axis of abscissa 40 indicative of time and an axis of ordinate 42 indicative of blood pressure. Bars 44 are continuously displayed on the two-dimensional table 40, 42, as shown in the graph of FIG. 3. Each bar 44 represents a corresponding one of optimum pulses M2, . . . , and an upper and a lower point A and B of each bar 44 corresponds to maximum and minimum blood pressure of the subject, respectively.

The CPU 28 receives pulse signal CK from a pulse signal generator 46 at a predetermined frequency.

Figure 4:
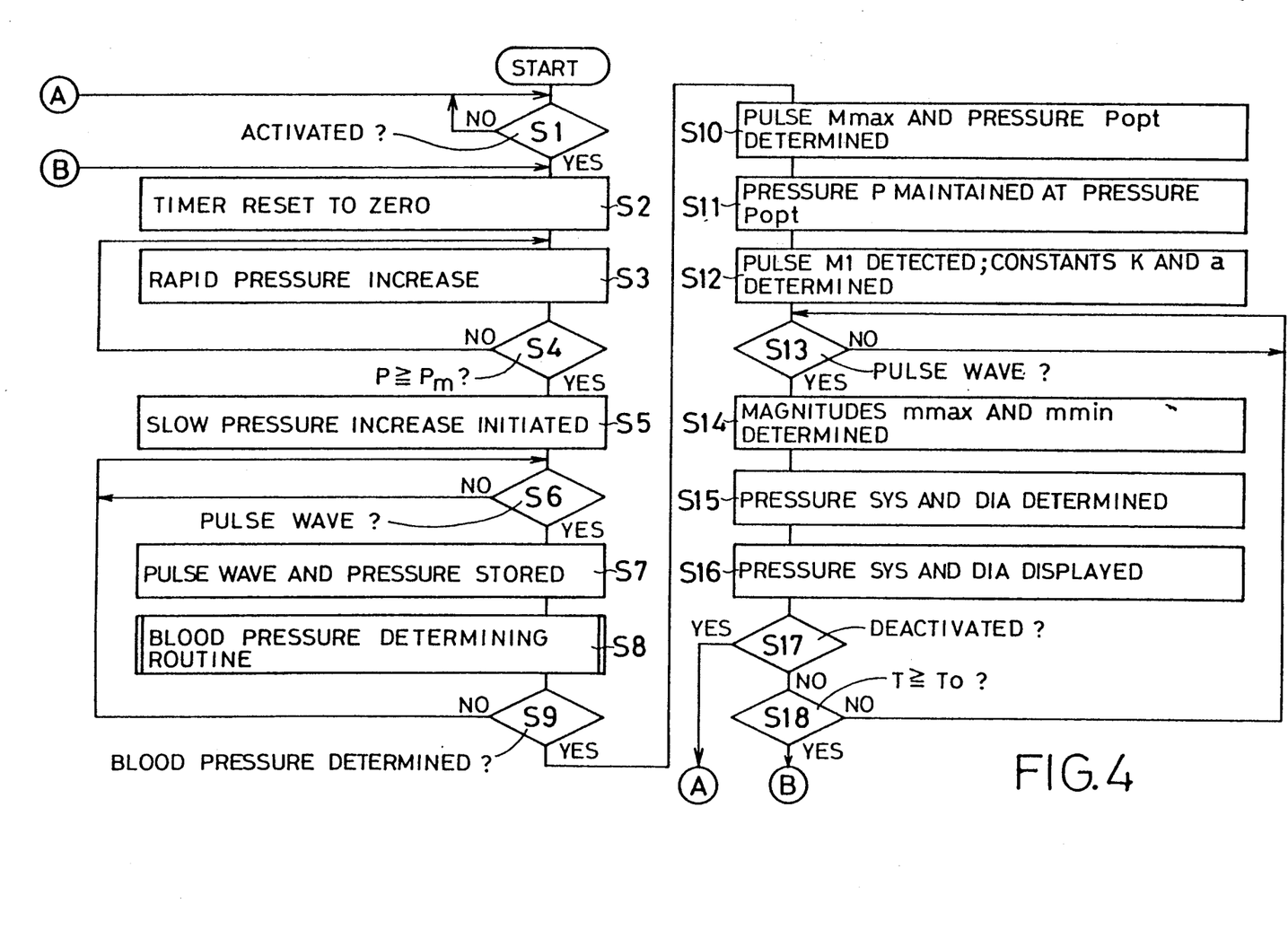
FIG. 4 is a flow chart illustrating the operation of the apparatus of FIG. 1.

Referring next to FIG. 4, there is illustrated the flow chart according to which the present apparatus is operated to monitor blood pressure of the subject.

Upon operation of a power switch (not shown) to apply electric power to the apparatus, the control of the CPU 28 goes to step S1 at which it is judged whether or not an activation switch (not shown) has been operated to generate activation signal to the CPU 28, namely, whether or not activation signal is present at the CPU 28. If the pulse wave detecting probe 10 is fixed on the wrist surface 13 with the wrist band 14 wound and fastened around the wrist 11 and the activation switch is operated, the control of the CPU 28 goes to step S2 at which content or count T of a timer of the microcomputer is rest to zero, so that the timer starts counting the number of pulse signals CK supplied from the pulse signal generator 46.

Step S2 is followed by step S3 at which the electric pump 22 is activated and the pressure-regulating valve 24 is placed in the rapid-inflation position, so that pressure P in the fluid-tight space 17 is increased at the high rate. Step S3 is followed by step S4 at which it is judged whether or not pressure P has reached target level Pm. If the judgement at step S4 is negative (NO), the control of the CPU 28 goes back to step S3. On the other hand, if the judgement at step S4 is affirmative (YES), then step S4 is followed by step S5 at which the valve 24 is placed to the slow-inflation position so as to increase pressure P at the slow rate. Thus, the pulse wave sensor 18 is pressed against the radial artery 12 with a continuously variable pressing force.

Step S5 is followed by step S6 at which a pulse of pulse wave has been detected by the pulse wave sensor 18. If the judgement at step S6 is negative, step S6 is repeated until the judgement is turned affirmative. Meanwhile, if the judgement at step S6 is affirmative, the control of the CPU 28 goes to step S7 at which the magnitude (i.e., amplitude) of the pulse detected at step S6 and the pressure P of the fluid-tight space 17 corresponding to the detected pulse, are stored in the RAM 30. Similarly, the magnitude (i.e., amplitude) of following pulses and the corresponding pressures P are timewise stored in the RAM 30. In the present embodiment, step S5 stored in the form of software program in the ROM 32 and the CPU 28 and the RAM 30 for effecting step S5, serve as a part of the means for pressing the pulse wave sensor against the arterial vessel with the continuously variable pressing force.

Step S7 is followed by step S8 at which actual maximum and minimum blood pressure H, L of the subject are determined based on variation in magnitudes (amplitudes) of the pulses of the pulse wave stored in the RAM 30, and the determined blood pressure H, L are stored in the RAM 30. The blood pressure determining algorithm effected at step S8 consists, for example, of selecting, from sequential pairs of the time-wise stored pulses, two pairs of adjacent pulses each of which pairs provides a maximum value with respect to amplitude difference (absolute value), determining a pressure in the fluid-tight space 17 at the time of detection of one pulse of each pair which one pulse has a smaller amplitude than the other pulse and determining maximum and minimum blood pressure of the subject according to a predetermined relationship between blood pressure and pressure P of the fluid-tight space 17 based on the determined two pressures of the fluid-tight space 17. The higher one of the two pressures of the fluid-tight space 17 corresponds to the maximum blood pressure, while the lower one corresponds to the minimum blood pressure. In the present embodiment, step S8 stored in the ROM 32 and the CPU 28 and the RAM 32 for effecting step S8 serve as the means for determining actual blood pressure of the subject.

Step S8 is followed by step S9 at which it is judged whether or not the determination of actual blood pressure has been terminated, namely, maximum and minimum blood pressure of the subject has been determined at a current cycle. At an early stage of each cycle the judgement at step S9 is found negative, because a sufficient number of pulses to determine maximum and minimum blood pressure have not been detected yet at the stage. Meanwhile, if the judgement at step S9 is turned affirmative, the control of the CPU 28 goes to step S10.

At step S10 a maximum pulse $M_{max}$ having a maximum amplitude is selected from all the pulses of pulse wave detected and stored while pressure P is continuously increased at the slow rate, and a pressure of the fluid-tight space 17 at the time of detection of maximum pulse $M_{max}$ is determined as optimum pressure $P_{opt}$. Step S10 is followed by step S11 at which the pressure-regulating valve 24 is placed from the slow-inflation position to the rapid-deflation position so as to decrease pressure P at the high rate to optimum pressure $P_{opt}$ and subsequently placed in the holding position so as to maintain pressure P at optimum pressure $P_{opt}$. In the present embodiment step 10 stored in the ROM 32 and the CPU 28 and the RAM 30 for effecting step S10 serve as the means for selecting the maximum pulse. Meanwhile, step S11 stored in the ROM 32 and the CPU 28 and the RAM 32 for effecting step S11 serve as the means for maintaining the pressing force of the pressing means at the optimum force at which the maximum pulse has been detected by the pulse wave sensor.

Step S11 is followed by step S12 at which first optimum pulse M1 is detected by the pulse wave sensor 18 and stored in the RAM 30. First optimum pulse M1 has substantially the same amplitude as that of maximum pulse $H_{max}$, because the sensor 18 is pressed against the radial artery 12 with pressure P in the fluid-tight space 17 maintained at optimum pressure $P_{opt}$. Also, a maximum and a minimum magnitude $m1_{max}$, $m1_{min}$ of pulse M1 are determined, and the determined values $m1_{max}$, $m1_{min}$ are utilized to determine a BP-PM relationship (relationship between blood pressure and pulse magnitude) according to which maximum and minimum blood pressure of the subject is continuously estimated. The BP-PM relationship is expressed by the following equations:

$$SYS = K \cdot m_{max} + a \tag{1}$$

$$DIA = K \cdot m_{min} + a \tag{2}$$

, where
SYS: maximum blood pressure of the subject,
DIA: minimum blood pressure of the subject,
K, a: constants,
$m_{max}$: maximum magnitude of each of optimum pulses M1, M2, M3, ...,
$m_{min}$: minimum magnitude of each of optimum pulses M1, M2, M3, ....

Constants K, a are determined by replacing values SYS, DIA with actual maximum and minimum blood pressure H, L, respectively, and replacing values $m_{max}$, $m_{min}$ with values $m1_{max}$, $m1_{min}$ of first optimum pulse M1. The pair of equations (1), (2) are determined and utilized on the assumption that maximum and minimum blood pressure are directly proportional to maximum and minimum magnitudes of a pulse of pulse wave, respectively. The pair of equations (1), (2) represent a single linear function or a straight line. Provided that the straight line expressed by the equations (1), (2) is drawn in an X-Y two-dimensional table defined by an X axis indicative of pulse magnitude and a Y axis indicative of blood pressure, constants K, a correspond to the slope and y-intercept of the line, respectively. Due to the y-intercept a, blood pressure is not always at zero even if pulse magnitude is at zero. In the present embodiment, step S12 stored in the ROM 32 and the CPU 28 and the RAM 30 for effecting step S12 serve as the means for determining the BP-PM relationship.

Step S12 is followed by step S13 at which it is judged whether or not second optimum pulse M2 following pulse M1 has been detected by the pulse wave sensor 18. If the judgement at step S13 is affirmative, step S13 is followed by step S14 at which second optimum pulse M2 is stored and a maximum and a minimum magnitude $m2_{max}$, $m2_{min}$ of second optimum pulse M2 are determined. At the following step S15 values $m_{max}$, $m_{min}$ in the equations (1), (2) are replaced with values $m2_{max}$, $m2_{min}$ of pulse M2, so that maximum and minimum blood pressure SYS, DIA corresponding to pulse M2 are estimated. Step S15 is followed by step S6 at which the thus estimated blood pressure SYS, DIA are displayed on the display device 38.

Step S16 is followed by step S17 at which it is judged whether or not the activation switch (not shown) has been operated again. If the judgement at step S17 is affirmative, the control of the CPU 28 goes back to step S1. On the other hand, if the judgement is negative, the control goes to step S18 at which content T of the timer is compared with a reference value To. Reference value To represents a regular time interval corresponding to a predetermined cycle time of repetitive cycles. A BP-PM relationship is determined at each cycle to replace the relationship determined at the preceding cycle. Thus, constants K, a are re-determined at step S12 of each cycle. In other words, the BP-PM relationship is repetitively adjusted at the regular time intervals, so as to maintain the accuracy of determination of blood pressure. Reference value To falls in the range of 5 to 10 minutes, for example. Accordingly, if the judgement at step S18 is affirmative, namely, if count T has reached reference value To, the control of the CPU 28 returns to step S2. Since second optimum pulse M2 has just been detected at present, the judgement at step S13 must be negative at the time, and the control goes back to step S13 and the following steps so as to determine and display values SYS, DIA based on each of optimum pulses M3, M4, . . . following second optimum pulse M2. Thus, values SYS, DIA are continuously displayed in the form of bars 44 on the display device 38. In the present embodiment, steps S14 and S15 stored in the ROM 32 and the CPU 28 and the RAM 30 for effecting those steps serve as the means for continuously determining blood pressure of the subject according to the BP-PM relationship based on magnitudes of the optimum pulses of pulse wave detected by the pulse wave sensor pressed against the arterial vessel with the optimum force.

If the judgement at step S18 is turned affirmative while steps S13-S18 are repeated again and again, the control of the CPU 28 returns to step S2 and the following steps. Specifically, another actual maximum and minimum blood pressure H, L are determined at step S8, and another pair of maximum and minimum magnitudes $m1_{max}$, $m1_{min}$ of first optimum pulse M1 are determined at step S12. By using the newly determined values H, L and values $m1_{max}$, $m1_{min}$, another pair of constants K, a, namely, another pair of equations (1), (2) are determined. Thus, a new BP-PM relationship is determined. The new BP-PM relationship is utilized to continuously estimate maximum and minimum blood pressure SYS, DIA based on maximum and minimum magnitudes of each of optimum pulse which are detected by the pulse wave sensor 18 pressed against the radial artery 12 with pressure P held at optimum pressure $P_{opt}$ determined at step S10 of the current cycle. The thus determined blood pressure values SYS, DIA are timewise displayed on the display device 38.

As is apparent from the foregoing, in the present embodiment, actual maximum and minimum blood pressure H, L are determined in the blood pressure determining routine of step S8, based on variation in magnitude of pulse wave which are detected by the pulse wave sensor 18 while pressure P in the fluid-tight space 17 of the housing 16 is increased at the slow rate. Meanwhile, maximum pulse $M_{max}$ having a maximum amplitude is selected from all the pulses of pulse wave that are detected by the sensor 18 while pressur P is continuously increased at the slow rate, and optimum pressure $P_{opt}$ in the fluid-tight space 17 at the time of detection of maximum pulse $M_{max}$ is determined. Thus, pressure P is maintained at optimum pressure $P_{opt}$, so that optimum pulses each having substantially the same amplitude as that of maximum pulse $M_{max}$ are detected by the pulse wave sensor 18. At step S12 a BP-PM relationship is determined based on actual blood pressure H, L and magnitudes $m1_{max}$, $m1_{min}$ of first optimum pulse M1, and at step S14 blood pressure of the subject is continuously determined according to the BP-PM relationship based on magnitudes of the optimum pulses M2, M3, . . . .

According to the principle of the present invention, it is unnecessary to employ an inflatable cuff for measuring blood pressure of the subject, in contrast to conventional blood pressure measuring devices using an inflatable cuff. In the invention, blood pressure is determined based on the magnitude variation of pulse wave detected by the pulse wave sensor 18. Thus, if the method or apparatus according to the invention is used to measure blood pressure, it is unnecessary to wind and set an inflatable cuff around an upper arm or other body portions of the subject. Further, the present invention offers an advantage that blood pressure measurement is free from adverse influences of noise which may be produced by, for example, physical motion of the subject.

In the illustrated embodiment, actual blood pressure is measured at each of repetitive cycles or regular time intervals, and the BP-PM relationship, according to which blood pressure is continuously determined, is adjusted at each cycle. Stated differently, a BP-PM relationship determined at a cycle is replaced with another BP-PM relationship determined at the following cycle. Thus, the present blood pressure monitoring apparatus permits accurate blood pressure measurement. Also the monitoring is effected without congestion and with extremely reduced unconfortable feeling in the subject, even in the case of a comparatively long-time monitoring, in contrast to the conventional devices using an inflatable cuff which continues to be wound around an upper arm of a subject during a monitoring period.

In the illustrated embodiment, a maximum pulse $M_{max}$ having a maximum amplitude is selected from all the pulses that are detected by the pulse wave sensor 18 while pressure P in the fluid-tight space 17 (housing 16) is continuously increased, and a pressure of the space 17 at the time of detection of maximum pulse $M_{max}$ is determined as optimum pressure $P_{opt}$. The pulse wave sensor 18 is pressed against the radial artery 12 with pressure P maintained at optimum pressure $P_{opt}$. In this condition, optimum pulses (M1, M2, M3, ... ) having substantially the same amplitude as that of maximum pulse $M_{max}$ are detected by the pulse wave sensor 18. A BP-PM relationship, i.e., constants K, a are determined based on first optimum pulse M1 together with actual blood pressure, and blood pressure of the subject is continuously determined according to the BP-PM relationship based on magnitudes of optimum pulses M2, M3, ... following optimum pulse M1. Thus, the present apparatus is capable of monitoring blood pressure of the subject with satisfactory accuracy.

While the present invention has been described in its presently preferred embodiment with detailed particularities, the invention may be embodied with various modifications.

For example, although the illustrated apparatus of FIG. 1 is of the type which continuously determines and displays blood pressure of a subject at each of repetitive cycles, the concept of the present invention is applicable to a blood pressure measuring apparatus of a type which effects a single blood pressure measurement upon each operation of an activation switch thereof. The modified apparatus, which may have a construction similar to that of the apparatus of FIG. 1, is operated according to the same steps as steps S1-S9 of the flow chart of FIG. 4, each time the activation switch is operated. In this case, blood pressure of the subject is determined based on variation in magnitude of pulse wave detected by the pulse wave sensor 18, and accordingly it is unnecessary to use an inflatable cuff. Thus, the modified apparatus eliminates the cumbersome activities of winding and fixing the inflatable cuff around an upper arm of a subject, and permits blood pressure measurement without influences of noise caused by physical motion of the subject.

While in the illustrated embodiment, the BP-PM relationship is determined based on first optimum pulse M1 together with actual blood pressure, it is possible to determine the BP-PM relationship based on a magnitude of maximum pulse $M_{max}$, a magnitude of one of other optimum pulses than first optimum pulse M1, or an average of magnitudes of two or more of maximum pulse $M_{max}$ and optimum pulses M1, M2, ....

While in the illustrated embodiment actual blood pressure H, L is determined, after pressure P is increased to target level Pm at the comparatively high rate, based on the pulse wave which is detected by the pulse wave sensor 18 while pressure P is continuously increased at the comparatively low rate, it is possible to determine actual blood pressure H, L, after pressure P is increased at a comparatively high rate up to about 180 mmHg which level is higher than an estimated maximum blood pressure of the subject, based on the pulse wave detected by the sensor 18 while pressure P is then decreased at a comparatively low rate of 5 to 6 mmHg/sec. Further, it is possible to determine actual blood pressure H, L, without providing target pressure Pm, based on the pulse wave detected by the sensor 18 while pressure P is increased from zero mmHg at the comparatively low rate.

While in the illustrated embodiment both maximum and minimum blood pressure of the subject are determined and displayed, it is possible to determine and display one of maximum and minimum blood pressure, or average blood pressure of maximum and minimum blood pressure.

Although in the illustrated embodiment pulse wave is detected from the radial artery 12, the blood pressure monitoring apparatus may be adapted to detect pulse wave from other arterial vessels which extend near body surface of the subject and accordingly permit pulse wave to be easily detected therefrom, such as a carotid artery and a dorsal pedal artery.

While in the illustrated embodiment the BP-PM relationship is determined on the assumption that blood pressure is directly proportional to magnitude of pulse wave, blood pressure may be defined as a quadratic function of pulse wave magnitude and therefore the BP-PM relationship may be expressed by a quadratic function. Alternatively, it is possible that the BP-PM relationship be determined by selecting one out of a plurality of pre-stored maps each representing a relationship between blood pressure and pulse wave magnitude, based on actually measured blood pressure and actually detected pulse wave magnitude.

While in the illustrated embodiment the BP-PM relationship is defined by both of constants K (slope) and a (y-intercept), it is possible to define the relationship simply by the slope K. It is possible to determine different slopes $K_{sys}$, $K_{dia}$ which are utilized to determine maximum and minimum blood pressure SYS, DIA, respectively, on the assumption that maximum blood pressure and a maximum magnitude of pulse have a proportional relationship therebetween different from a proportional relationship between minimum blood pressure and a minimum magnitude of pulse.

While in the illustrated embodiment blood pressure of the subject is continuously displayed in the form of bars 44 on the cathode ray tube of the display device 38, it is possible to concurrently record the blood pressure on a chart or other printing sheets. Other recording or displaying devices may be employed. Furthermore, the continuously determined blood pressure may be stored in memory means such as magnetic tape.

It is to be understood that the present invention may be embodied with other modifications, changes and improvements that may occur to those skilled in the art without departing from the scope and spirit of the invention defined in the appended claims.

What is claimed is:

1. A method of measuring a blood pressure of a subject by using a pulse wave sensor for detecting a pulse wave produced from an arterial vessel of the subject, pressing means for pressing the pulse wave sensor against the arterial vessel via a body surface of the subject, and means for detecting the magnitude of the pressing force of the pressing means, the method comprising the steps of:

pressing said pulse wave sensor against said arterial vessel with a continuously variable pressing force produced by said pressing means;

detecting variation in the magnitude of said pulse wave with said pulse wave sensor while the pressing force of said pressing means is continuously varied;

detecting the magnitude of the pressing force of said pressing means; and determining an actual blood pressure of the subject, according to a predetermined relationship between blood pressure and the pressing force of said pressing means, based on the detected magnitude variation of the pulse wave and the detected magnitude of the pressing force of said pressing means.

2. The method as set forth in claim 1, wherein said pulse wave consists of a plurality of pulses, the step of detecting variation in magnitude of the pulse wave consists of detecting an amplitude of each of the pulses of the pulse wave.

3. The method as set forth in claim 2, wherein the step of determining a blood pressure of the subject comprises selecting, from sequential pairs of the detected pulses of the pulse wave in the order of detection of the pulses, two pairs of pulses each of which pairs provides a maximum value with respect to amplitude difference, determining a pressing force of said pressing means at a time of detection of one of said each pair of pulses which one pulse has a smaller amplitude than the other pulse of said each pair, and determining maximum and minimum blood pressures of the subject based on the determined two pressing forces, according to said predetermined relationship between blood pressure and the pressing force of said pressing means.

4. A method of continuously measuring blood pressures of a subject by using a pulse wave sensor for continuously detecting a pulse wave produced from an arterial vessel of the subject, pressing means for pressing the pulse wave sensor against the arterial vessel via a body surface of the subject, and means for detecting the magnitude of the pressing force of the pressing means, the pulse wave consisting of a plurality of pulses, the method comprising the steps of:

pressing said pulse wave sensor against said arterial vessel with continuously variable pressing force produced by said pressing means;

detecting variation in the magnitudes of the pulses of said pulse wave with said pulse wave sensor while the pressing force of said pressing means is continuously varied;

detecting the magnitude of the pressing force of said pressing means;

determining an actual blood pressure of the subject according to a predetermined relationship between blood pressure and the pressing force of said pressing means, based on the detected magnitude variation of the pulses of the pulse wave and the detected magnitude of the pressing force of said pressing means;

selecting, from the detected pulses of the pulse wave, a maximum pulse having a maximum amplitude;

maintaining the pressing force of said pressing means at an optimum force at which said maximum pulse has been detected by said pulse wave sensor while said pressing force is continuously varied, so that said pulse wave sensor is pressed against said arterial vessel with said optimum force and thereby continuously detects optimum pulses of said pulse wave each of which has substantially the same amplitude as the maximum amplitude of said maximum pulse;

determining a relationship between blood pressure and pulse wave magnitude, based on the determined actual blood pressure and the magnitude of at least one pulse of said maximum pulse and said optimum pulses; and determining blood pressures of the subject continuously according to the thus determined relationship between blood pressure and pulse wave magnitude, based on the magnitudes of said optimum pulses.

5. The method as set forth in claim 4, wherein the step of determining a relationship between blood pressure and pulse wave magnitude consists of selecting a first one of said optimum pulses detected by said pulse wave sensor immediately after the pressing force of said pressing means is fixed at said optimum force and determining a relationship between blood pressure and pulse wave magnitude based on the determined actual blood pressure and a magnitude of said first optimum pulse.

6. The method as set forth on claim 4, further comprising the step of repeating the step of pressing said pulse wave sensor, the step of detecting variation in magnitude of pulses of said pulse wave, the step of determining an actual blood pressure of the subject, the step of selecting a maximum pulse, the step of maintaining the pressing force at an optimum force, and the step of determining a relationship between blood pressure and pulse wave magnitude, such that, at each of a plurality of repetitive cycles defined by said repeating step, the relationship determined at each cycle is replaced with the relationship determined at a cycle following each said cycle, and the step of continuously determining blood pressure of the subject according to a currently effective one of the repetitively determined relationships is effected.

7. The method as set forth in claim 6, wherein said plurality of repetitive cycles produced by said repeating step have a predetermined time, each of said repetitively determined relationships determined during said repeating step being effective during said predetermined cycle time, said predetermined cycle time falling in a range of 5 to 10 minutes.

8. The method as set forth in claim 4, wherein the step of determining an actual blood pressure of the subject consists of determining actual maximum and minimum blood pressures of the subject, the step of determining a relationship between blood pressure and pulse wave magnitude consists of determining a relationship between blood pressure and pulse wave magnitude based on the actual maximum and minimum blood pressures and a maximum and a minimum magnitude of at least one pulse of said maximum pulse and said optimum pulses, and the step of continuously determining blood pressure of the subject comprises continuously determining maximum and minimum blood pressures of the subject according to the determined relationship based on maximum and minimum magnitudes of said optimum pulses.

9. The method as set forth in claim 8, wherein the step of determining a relationship between blood pressure and pulse wave magnitude, said relationship being expressed as follows $$SYS = K^* m_{max} + a$$

$$DIA = K^* m_{min} + a$$

, where
SYS: said maximum blood pressure of the subject,
DIA: said minimum blood pressure of the subject,
K, a: constants,
$m_{max}$: said maximum magnitude of each of said optimum pulses, and
$m_{min}$: said minimum magnitude of each of said optimum pulses,
consists of determining the values of said constants K, a by replacing the values SYS, DIA with said determined actual maximum and minimum blood pressure, respectively, and replacing the values $m_{max}$, $m_{min}$ with said maximum and minimum magnitude of said at least one pulse of said maximum pulse and said optimum pulses, respectively.

10. An apparatus for measuring a blood pressure of a subject, comprising:

a pulse wave sensor for detecting a pulse wave produced from an arterial vessel of the subject;

pressing means for providing a pressing force for pressing said pulse wave sensor against said arterial vessel via a body surface of the subject;

said pulse wave sensor detecting variation in the magnitude of said pulse wave while the pressing force of said pressing means is continuously varied;

means for detecting the magnitude of the pressing force of said pressing means; and means for determining an actual blood pressure of the subject according to predetermined relationship between blood pressure and the pressing force of said pressing means, based on the detected magnitude variation of the pulse wave and the detected magnitude of said pressing force.

11. An apparatus for measuring blood pressures of a subject, comprising:

a pulse wave sensor for continuously detecting a pulse wave produced from an arterial vessel of the subject, said pulse wave consisting of a plurality of pulses;

pressing means for providing a pressing force for pressing said pulse wave sensor against said arterial vessel via a body surface of the subject, said pressing means providing a continuously variable pressing force;

said pulse wave sensor detecting variation in the magnitudes of the pulses of said pulse wave while the pressing force of said pressing means is continuously varied;

means for detecting the magnitude of the pressing force of said pressing means;

first means for determining an actual blood pressure of the subject according to a predetermined relationship between blood pressure and the pressing force of said pressing means, based on the detected magnitude variation of the pulses of the pulse wave and the detected magnitude of the pressing force of said pressing force;

second means for selecting, from the detected pulses of the pulse wave, a maximum pulse having a maximum amplitude;

third means for maintaining the pressing force of said pressing means at an optimum force at which said maximum pulse has been detected by said pulse wave sensor while said pressing force is continuously varied, so that said pulse wave sensor is pressed against said arterial vessel with said optimum force and thereby continuously detects optimum pulses of said pulse wave each of which has substantially the same amplitude as the maximum amplitude of said maximum pulse;

fourth means for determining a relationship between blood pressure and pulse wave magnitude, based on the determined actual blood pressure and the magnitude of at least one pulse of said maximum pule and said optimum pulses; and fifth means for continuously determining blood pressures of the subject according to the determined relationship between blood pressure and pulse wave magnitude, based on the magnitudes of said optimum pulses.

12. The apparatus as set forth in claim 11, wherein said fourth means comprises:

means for detecting a first optimum pulse, said first optimum pulse being detected by said pulse wave sensor immediately after the pressing force of said pressing means is fixed at said optimum force; and means for determining said relationship based on the determined actual blood pressure and a magnitude of said first optimum pulse.

13. The apparatus as set forth in claim 11, further comprising means for determining a plurality of repetitive cycles, wherein, during each of said repetitive cycles, said pressing means presses said pulse wave sensor at said each cycle, said pulse wave sensor detects the magnitude variation of the pulses of the pulse wave at said each cycle, said first means determines said actual blood pressure at said each cycle, said second means selects said maximum pulse at said each cycle, said third means maintains said pressing force at said each cycle, said fourth means determines said relationship at said each cycle, the relationship determined at said each cycle being replaced with the relationship determined at a cycle following said each cycle, and said fifth means continuously determines the blood pressure of the subject according to a currently effective one of the repetitively determined relationships.

14. The apparatus as set forth in claim 13, wherein said plurality of repetitive cycles have a predetermined cycle time, each of said repetitively determined relationships being effective during said predetermined cycle time, said predetermined cycle time falling in a range of 5 to 10 minutes.

15. The apparatus as set forth in claim 11, wherein said pressing means comprises a housing in which said pulse wave sensor is accommodated, an elastic diaphragm disposed between said housing and said pulse wave sensor such that said pulse wave sensor is supported by said elastic diaphragm and that said elastic diaphragm cooperates with said housing to define a fluid-tight space in said housing, an electic pump for supplying said fluid-tight space with pressurized fluid so as to increase pressure in said fluid-tight space, and a pressure-regulating valve for regulating said pressurized fluid in said fluid-tight space and thereby regulating the pressure of said fluid-tight space, said elastic diaphragm pressing said pulse wave sensor against said arterial vessel via said body surface while the pressure of said fluid-tight space is continuously varied, the pressure of said fluid-tight space serving as the pressing force of said pressing means.

16. The apparatus as set forth in claim 15, wherein said pressing means further comprises means for continuously increasing said pressure in said fluid-tight space whereby said pulse wave sensor detects the magnitude variation of the pulses of the pulse wave while the pressure of said fluid-tight space is continuously increased from 40 mmHg at a rate of 5 to 6 mmHg per second.

17. The apparatus as set forth in claim 15, wherein said pressing means comprises means for continuously decreasing said pressure of said fluid-tight space whereby said pulse wave sensor detects the magnitude variation of the pulses of the pulse wave while the pressure of said fluid-tight space is continuously decreased from 180 mmHg at a rate of 5 to 6 mmHg per second.

18. The apparatus as set forth in claim 11, wherein said pressing means further comprises means for terminating the continuous variation of the pressing means after said actual blood pressure is determined by said first means.

19. The apparatus as set forth in claim 11, further comprising means for continuously displaying the blood pressures of the subject determined by said fifth means.

* * * * *